United States Patent [19]

Bengtsson

[11] 4,271,854

[45] Jun. 9, 1981

[54] TEETH CLEANING IMPLEMENT

[76] Inventor: Sigurd W. Bengtsson, Bruksgatan 17, 41451 Göteborg, Sweden

[21] Appl. No.: 27,500

[22] Filed: Apr. 5, 1979

[30] Foreign Application Priority Data

Apr. 18, 1978 [SE] Sweden .................. 7804291

[51] Int. Cl.³ ............................................. A61C 15/00
[52] U.S. Cl. ......................................................... 132/89
[58] Field of Search ...................................... 132/89, 93

[56] References Cited

U.S. PATENT DOCUMENTS

| 435,350 | 8/1890 | Oehlecker | 132/90 |
| 1,654,230 | 12/1927 | Zimmerman | 132/89 |
| 2,527,857 | 10/1950 | Strachan | 132/93 |
| 3,672,378 | 6/1972 | Silverman | 132/93 |
| 3,954,115 | 5/1976 | Bengtsson | 132/89 |

Primary Examiner—Gregory E. McNeill
Attorney, Agent, or Firm—Hill, Van Santen, Steadman, Chiara & Simpson

[57] ABSTRACT

An implement suited for cleaning also interproximal faces at the molars is made of pliable material, and includes a middle portion and two tapering end portions issuing therefrom. The middle portion is formed with a cross section to make it substantially rigid in use, and the end portions are bent in the same direction with respect to the middle portion.

The end portions have a triangular cross section adjacent to the middle portion and taper towards the distal ends, where the end portions are very slim compared with the cross section adjacent to the middle portion. At least the side face of the each end portion turned inwards at the bend is roughened.

5 Claims, 5 Drawing Figures

U.S. Patent   Jun. 9, 1981   4,271,854
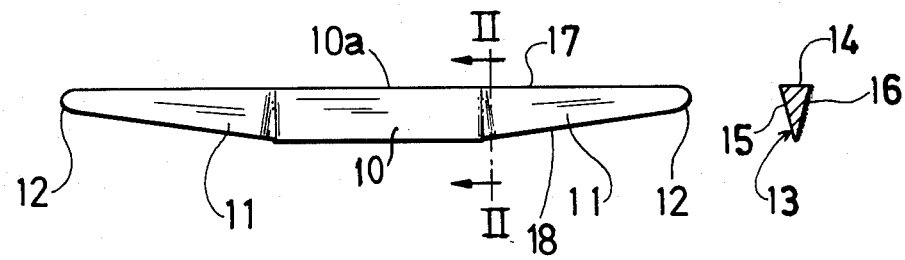
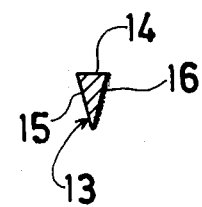
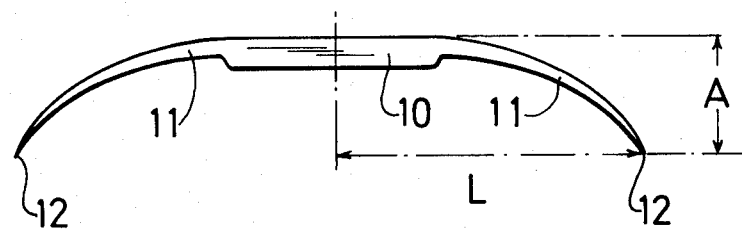
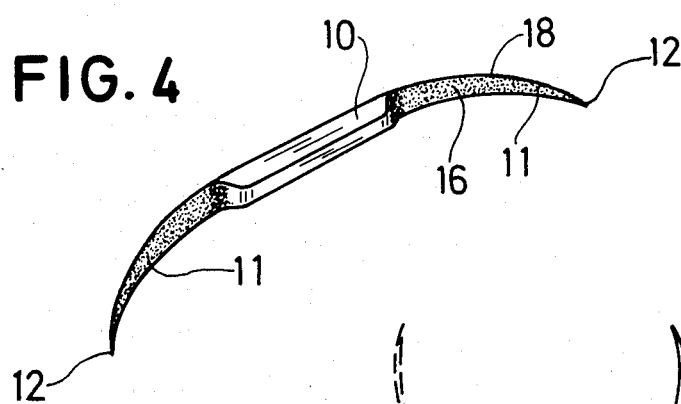
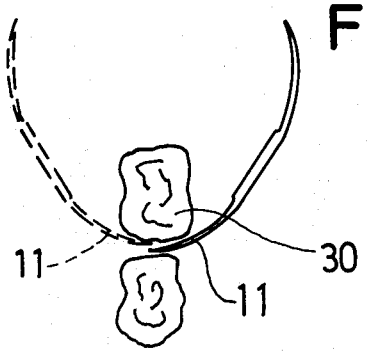

TEETH CLEANING IMPLEMENT

BACKGROUND OF THE INVENTION

1. Field of the Invention

This invention relates to a plastic toothpick.

2. Prior Art

A thorough oral hygiene necessitates, beside a methodical brushing, also the removal of foreign matter lodged in the spaces between the teeth. To that end toothpicks of various designs have been proposed, some of which have furthermore been formed so as to make possible a certain working of the teeth faces.

The intent is to remove the coating, called plaque, which adheres to the teeth and which would cause damage thereto.

It is possible to obtain satisfactory results with conventional straight teeth cleaning implements, i.e. toothpicks formed so as to permit a cleaning action in addition to mere picking, when the front teeth and also the outer parts of interproximal faces at the molars are concerned. The inward parts of said interproximal faces are more difficult to reach, and for the treatment of those faces straight implements will not provide a satisfactory result.

SUMMARY OF THE INVENTION

The present invention refers to implements suitable for cleaning all kinds of interproximal faces for removing occasional particles or more permanent coatings, such as early stages of tartar scale. The implement is formed so as to permit a safe grip so the implement may be introduced into difficult passages with the necessary force, in the upper jaw as well as in the lower jaw, and which may be used at the left hand side as well as at the right hand side of the mouth, as the need may be. For the cleaning function it is not a question of picking, i.e. a movement in the plane of the interspace, but of a reciprocatory movement during a successive change of the angular position in relation to said plane, so a proximal face of a tooth may be fully treated during a cleaning operation.

An implement according to the invention comprises gradually tapering end portions, extending to both sides, and being bent away from a middle plane through the implement, and has a middle portion of the implement shaped like a substantially prismatic body, having a sufficient cross section to make it substantially rigid in use, the end portions issuing from said middle portion being bent in the same direction with respect to the middle portion, and adjacent to the latter having a cross section equalling an isosceles triangle, where the equal sides are noticeably longer than the base of the triangle, the end portions being further so formed that the base as well as the sides will decrease in the direction of the distal end of the pertaining end portion.

The side of each end portion corresponding to the base of the cross section triangle extends along a substantially straight line from the middle portion to the distal end, and is smooth all along its extent, while at least the side forming the concave face of an end portion is roughened.

The arc of an end portion is preferably selected so its distal end will be located at a distance from the plane of the middle portion corresponding to about one fourth of the total length of the implement.

BRIEF DESCRIPTION OF THE DRAWING

FIG. 1 is an elevational view of an implement according to the invention,

FIG. 2 is a view of a cross sectional slice taken along line II—II in FIG. 1,

FIG. 3 is a bottom view thereof as viewed from its "base" side,

FIG. 4 is a perspective view of the implement resting on its "base side", and

FIG. 5 indicates how the implement is to used.

DESCRIPTION OF A PREFERRED EMBODIMENT

The implement is made of a comparatively pliable material of the type suitable for injection molding. Components of this kind are manufactured in multiple cavity molds.

An implement according to the invention comprises a middle portion 10, and two end portions 11 issuing to opposite directions therefrom and tapering towards distal ends 12.

The injection of the material preferably occurs at the middle portion 10 and which is formed as a prismatic body of sufficient cross section to make it substantially rigid in use so as to provide a safe grip at the center of the implement.

Each end portion 11 has, adjacent to the middle portion 10, a cross section equalling an isosceles triangle 13 (FIG. 2), which is defined by a base 14 and two equally long sides 15 and 16. The latter are noticeably longer than the base 14, preferably about twice as long as the latter. The height as well as the base are gradually reduced in the direction of the distal end 12 of the portion 11.

The edge face 17 (FIG. 1) of an end portion, corresponding to the base 14 of the triangle, runs substantially straight from one base plane 10a of the middle portion 10 to the distal end 12, and has a smooth face. This edge face will, in use, always be turned towards the gum.

The ridge 18 formed by the converging side faces 15 and 16 will thus extend from the middle portion 10 sloping towards the distal end 12. The end portion here, to about one-fifth of the length of the end portion 11, is very slim and will thus facilitate being introduced into narrow spaces. The distal end, itself, is smoothly rounded so as not to damage the gum tissue.

The two end portions 11 (FIG. 3) are bent in the same direction with respect to the middle portion 10. The length L of an end portion 11 is selected with respect to what practice has shown necessary with conventional toothpicks, and the arc is selected so the distal end 12 will be located at a distance A from a base plane of the middle portion about corresponding to one-fifth to one-fourth of the total length of the implement.

The inwardly turned (concave) faces are roughened, for instance by spark erosion of the corresponding faces of the injection mold, while the faces corresponding to the base 14, and usually also the other side face remain smooth.

The arc-form and the mirror-image configuration at the portions 11 make it possible to reach interproximal spaces in the upper jaw as well as in the lower jaw, and also to the left side as well as to the right side of the mouth. The plane base face 17 can always be turned towards the gum, and the roughened face at the concave side will provide a handy means for cleaning also difficult localized areas, at the inward ends of interproximal faces.

FIG. 5 schematically shows how the implement is to be turned to make possible an access to the remote face of a tooth 30 from both directions, whereby a full cleaning of this face is obtainable.

A further advantage of the preferred form is that the end portion of the implement, which at the moment is not in use, will enhance the grip. When the same is handled the inactive portion fits well between the thumb and the index finger. However the implement is turned, this portion will due to its resilient properties adapt itself to the fingers holding it, and the front end of the thumb and the index finger, respectively, will be firmly supported by the comparatively rigid middle portion, the position of which, thus, will be safely established. From the middle portion and outwards, the resiliency of the then active portion will influence the working upon the tooth.

What I claim is:

1. A cleaning implement, made of synthetic material, comprising:
   (a) a rigid middle 4-sided gripping portion; and
   (b) a pair of solid combined picking and scraping end portions extending integrally from opposite ends of said gripping portion, each of said end portions having an isosceles triangular cross-section, the sides of which being somewhat longer than the base of the triangle, the three sides of the triangular cross-section being straight, said end portions having a gradual curvature and taper from said gripping portion to their distal ends, the curvatures being in the same direction, and one of the lateral sides of each said end portions having a roughened surface, whereby the curved portions may be selectively inserted into the interproximal interstices in the upper and in the lower jaw at both sides of the mouth with the flat base of the curved portion disposed against the gum, and in each instance with the implement extending forwardly out of the mouth.

2. An implement according to claim 1, the curvature of each end portion being such that its distal end has an offset (A) from the remote side face of said middle portion which is about one-fifth to one-fourth of the total length of the implement.

3. An implement according to claim 1, the side face of both said end portions corresponding to the base of the triangle being smooth and lying in a plane common with one of the flat sides of said middle portion.

4. An implement according to claim 1, the side having the roughened surface lying on the concave side of said curvature.

5. An implement according to claim 1, the outermost one-fifth of each said end portion having the base of its triangular shape quite short as compared to the length of the base near said middle portion.

* * * * *